United States Patent [19]

Shapiro

[11] 3,955,930
[45] May 11, 1976

[54] AUTOMATIC DILUTOR HAVING COUPLED DILUENT AND REAGENT PLUNGERS

[76] Inventor: Justin Joel Shapiro, 1802 Second St., Berkeley, Calif. 94710

[22] Filed: Apr. 7, 1975

[21] Appl. No.: 565,569

[52] U.S. Cl. ............................. 23/259; 23/253 R; 73/425.6; 222/135; 222/137; 417/265
[51] Int. Cl.² ................... B01L 3/02; G01F 11/06
[58] Field of Search ..................... 23/259, 253 R; 73/425.6; 222/135, 137; 417/63, 250, 265

[56] References Cited
UNITED STATES PATENTS

| | | | |
|---|---|---|---|
| 3,197,285 | 7/1965 | Rosen | 73/425.6 X |
| 3,217,761 | 11/1965 | Shapiro | 141/27 |
| 3,484,207 | 12/1969 | Anthon | 73/425.6 X |
| 3,556,353 | 1/1971 | Echols | 417/63 X |
| 3,572,130 | 3/1971 | Goldsmith | 23/259 X |
| 3,810,720 | 5/1974 | Lartigue et al. | 222/135 X |
| 3,837,534 | 9/1974 | Natelson | 222/137 |

Primary Examiner—Morris O. Wolk
Assistant Examiner—Arnold Turk
Attorney, Agent, or Firm—Herman L. Gordon

[57] ABSTRACT

An automatic dilutor consisting of an upstanding calibrated diluent barrel with a lower intake portion adapted to be supported in a diluent container and having an intake check valve. A main diluent plunger is provided in the barrel and develops suction when moved upwardly. The plunger has an enlarged top operating portion with a depending diluent-metering rod on which a diluent indicating lens is adjustably mounted, being engageable with a top flange on the barrel to limit extension of the plunger in accordance with the desired amount of diluent to be dispensed. A branch conduit connects the diluent barrel through another check valve with an upstanding calibrated reagent-aspirating barrel having an outlet conduit connected to its bottom portion. An aspirator plunger is provided in the aspirating barrel, the aspirator plunger having an enlarged top end with a depending reagent-metering rod on which another indicating lens is adjustably mounted, being engageable with a top flange on the aspirating barrel to limit extension of the aspirator plunger in accordance with the amount of reagent to be dispensed. The diluent indicating lens is yieldably connected to the reagent-metering rod so that the aspirator plunger will move upwardly only to its limit when the diluent plunger is moved upwardly to its limit, simultaneously drawing the preset desired amounts of diluent and reagent respectively into the diluent barrel and the aspirating barrel. When the diluent plunger is then moved downwardly to its bottom position, the connection between the diluent indicating lens and the reagent-metering rod causes the preset amounts of diluent and reagent to be simultaneously discharged through the outlet conduit.

15 Claims, 3 Drawing Figures

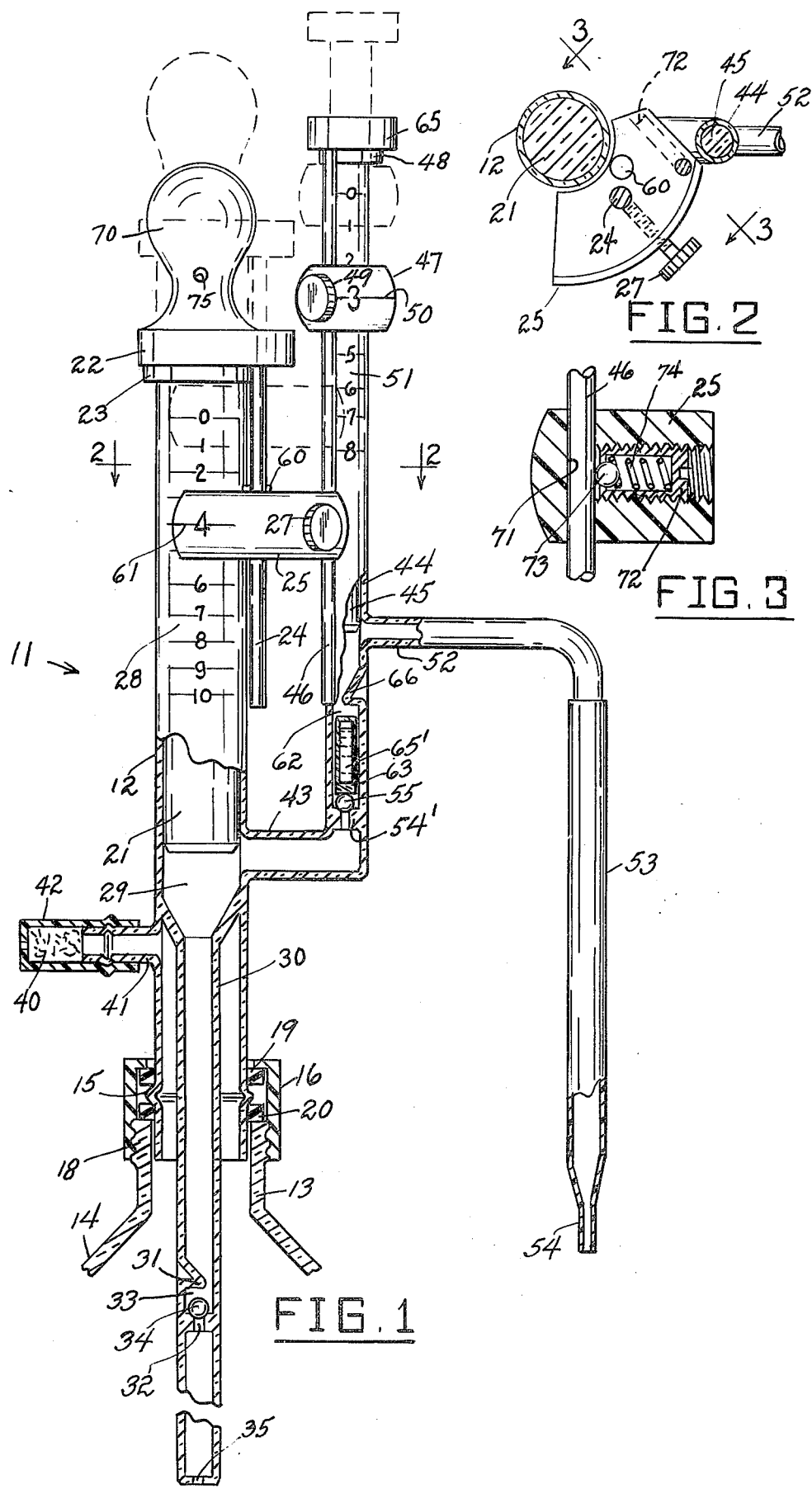

AUTOMATIC DILUTOR HAVING COUPLED DILUENT AND REAGENT PLUNGERS

This invention relates to liquid dispensing devices, and more particularly to a device for performing precise dilutions and which can be preset to dispense accurately measured proportions of reagent to diluent.

A main object of the invention is to provide a novel and improved device for withdrawing a precise amount of a liquid reagent from a supply vessel and simultaneously withdrawing another precise amount of a diluent liquid from a diluent container, and for then simultaneously discharging these precisely measured quantities of reagent and diluent into a receiving vessel, while at the same time washing out the delivery portion of the device with diluent, the operation of the device requiring only a single intake operating stroke followed by a single discharge stroke.

A further object of the invention is to provide an improved device for quickly and easily performing precise dilutions of one liquid with another, said device being simple in construction, being accurately settable for the desired dilutions, and being especially useful for rapidly performing precision repetitive dilutions.

A still further object of the invention is to provide an improved automatic dilutor for performing precise dilutions of one liquid with another, said dilutor being of a type which aspirates a precise amount of reagent from a supply vessel and simultaneously draws a precise amount of diluent from a diluent container, and then transfers the reagent together with the precisely measured amount of diluent to another vessel, the device being economical to manufacture, being easy to check visually for proper operation, being reliable in its action, being easy to keep clean, and being relatively compact in size.

A still further object of the invention is to provide an improved automatic precision dilutor of the type adapted to be mounted on a bottle or similar vessel containing diluent liquid and having a diluent barrel containing an operating plunger and an adjacent barrel containing a plunger arranged to draw a precisely measured amount of reagent from a reagent supply vessel, the operating plungers being coupled together in a manner such that they can be operated simultaneously without affecting the precision of the desired dilution.

Further objects and advantages of the invention will become apparent from the following description and claims, and from the accompanying drawings, wherein:

FIG. 1 is an elevational view, partly in vertical cross-section, of an improved automatic dilutor constructed in accordance with the present invention, shown mounted in operating position in the neck of a diluent bottle.

FIG. 2 is a horizontal cross-sectional view taken substantially on the line 2—2 of FIG. 1.

FIG. 3 is an enlarged vertical cross-sectional view taken substantially on the line 3—3 of FIG. 2.

A typical precision dilutor of the prior art is shown in U.S. Pat. No. 3,217,761 to Justin J. Shapiro. This prior art dilutor has a calibrated diluent barrel with an operating plunger and a calibrated reagent barrel, also with an operating plunger, these plungers being independently operated, so that the plungers must be separately reciprocated manually. Thus, the reagent plunger is first raised to draw the desired amount of reagent into the reagent barrel and the discharge tip, and then the reagent plunger is lowered to discharge said desired amount of reagent into a receiving vessel; then the diluent plunger is raised to draw the desired amount of diluent into the diluent barrel and is then lowered to discharge said desired amount of diluent into the receiving vessel. This involves four plunger strokes and is quite time-consuming. Also, because of the required four separate actuations, the prior art dilutor can be used only manually and is not adaptable to repetitive mechanical actuation. A prime purpose of the present invention is to reduce the number of required operating strokes to two, namely, to an upward filling stroke and a subsequent downward dispensing stroke, the single cycle being very easy to perform manually in a very short period of time and being such that it can be also rapidly performed by means of a suitable auxiliary mechanism, such as by a foot treadle-operated spring-biased linkage, whereby the operator's hands are free to attend to other related functions, such as to move the reagent supply container and the receiving vessels, as required. Furthermore, the reduction of required motions not only provides a saving in time and effort, but also reduces the chances of making mistakes in carrying out the dilution procedure.

Referring to the drawings, 11 generally designates an improved two-stroke precision dilutor constructed in accordance with the present invention. The dilutor 11 comprises a main tubular barrel 12 of relatively large diameter, of glass or other suitable transparent material, the lower end portion of the barrel being adapted to be sealingly mounted in the neck portion 13 of a bottle 14, or similar vessel, containing diluent liquid. Thus, said lower barrel portion may be provided with an integral circumferential sealing rib 15, and an internally threaded annular cap 16 may be threadedly engaged with the externally threaded upper portion 18 of neck 13, the rib 15 being received in the cap 16, with resilient deformable annular sealing rings 19 and 20 being provided on the barrel portion immediately above and below said rib, as shown in FIG. 1.

Sealingly and slidably mounted in the upper portion of barrel 12 is a diluent dispensing plunger 21 provided at its top end with the enlarged head flange 22, off center relative to the axis of the plunger, and being engageable with the outwardly projecting top flange or rim 23 of barrel 12 when the plunger is in its lowermost position, as shown in FIG. 1. A depending rod 24 is rigidly secured to the flange 22, extending parallel to and rightwardly adjacent to the barrel 12, as viewed in FIG. 1, and adjustably mounted on rod 24 is a transparent magnifying indicator block 25 which extends over a diluent volume scale 28 inscribed on barrel 12. Upward movement of indicator block 25 is limited by the barrel top flange 23, and a resilient deformable pad 60, of rubber, or the like, is secured on the top surface of block 25 in a position to engage with flange 23 so as to cushion the impact of block 25 with said flange. Indicator block 25 is provided with a clamping screw 27 to lock it in adjusted position on rod 24. Lens block 25 has an index line 61 to indicate the volumetric dispensing setting of the diluent plunger 21 relative to scale 28. Thus, the lens block may be adjusted on the rod 24 to deliver a predetermined amount of diluent per stroke from the diluent vessel 14, said volume being indicated on scale 28 by the index line 61 with the plunger in its fully lowered position, as shown in FIG. 1.

The plunger chamber, shown at 29, communicates with a reduced tubular conduit 30 formed integrally with barrel 12 and extending downwardly therefrom. The lower portion of conduit 30 is integrally formed with a ball valve chamber 33 containing a movable valve ball 34 which normally sealingly covers a valve port 32 but which is movable upwardly to engage a stop lug 31 responsive to suction developed by the upward movement of plunger 21, to allow diluent to flow upwardly into space 29. The bottom end of conduit portion 30 has a restricted diluent inlet aperture 35.

An outwardly extending air inlet tube 41 is integrally formed on the lower portion of barrel 12 immediately below the junction of the chamber 29 with the reduced conduit portion 30. An apertured cap 42 containing filter material 40 is secured on tube 41, said material 40 acting to filter the air drawn into diluent vessel 14 when diluent is dispensed therefrom, whereby to protect the diluent in the vessel 14 from contamination.

A horizontal branch tube 43 is formed integrally with barrel 12 and communicates with chamber 29 substantially at the level of the bottom end of plunger 21 when said plunger is in its lowermost position. Integrally formed with and rising vertically from the outer end of branch tube 43 is the reagent aspirating barrel 44, of relatively small diameter compared with barrel 12, containing the aspirating plunger 45. Plunger 45 is formed with the top flange 65 to which is rigidly secured a depending rod 46. Said rod 46 is provided with an adjustable transparent indicating lens block 47 engageable with the top rim flange 48 of barrel 44 to limit upward extension of plunger 45. Indicator block 47 has a locking screw 49 and an index line 50. A reagent intake volumetric scale 51 is inscribed on barrel 44, and the reagent intake volume may be preset by locking the lens block on the rod 46 with the plunger 45 fully lowered, namely, with the flange 65 engaging rim 48, the preset reagent volume being indicated by index line 50 on scale 51.

Integrally formed with the lower portion of barrel 44 is the laterally directed conduit portion 52 provided with the depending tip conduit member 53 having the reduced end portion 54. The origin of the laterally directed conduit 52 is at the level of the bottom end of plunger 45 when said plunger is fully lowered. Below the conduit portion 52, barrel 44 is formed with a cylindrical chamber 62 having an apertured valve ball seat 54' at its bottom end on which is movably disposed a sealing valve ball 55. A hollow weight vessel 63 is loosely disposed in chamber 62, engaging on ball 55, said weight vessel containing heavy material 65', such as mercury, tungsten, or the like. The vessel 63 is loosely and slidably disposed in chamber 62, allowing free flow of liquid therepast. Upward movement of the weighted vessel 63 is limited by the provision of an inwardly projecting stop lug 66 formed in the barrel 44 and being engageable by the top wall portion of the hollow vessel 63.

As will be presently explained, the purpose of the weighted vessel 63 is to aid in keeping the ball 55 sealingly engaged on the ball seat 54 when reagent is being aspirated into the device for subsequent delivery and dilution.

The contained volume of the conduit portion 52 and the tip portion 53 is preferably greater than the maximum capacity of the aspirating syringe defined by barrel 44 and plunger 45. This preferred relationship prevents the aspirated reagent from ever reaching the aspirating plunger 45.

An operating knob or handle 70 is rigidly secured on diluent plunger flange 22. Diluent plunger 21 is yieldably coupled to reagent plunger 45 so that reagent plunger 45 will rise to its limit when diluent plunger 21 is elevated to its limit. Thus, any suitable lost motion connection may be employed between the plungers. In the typical embodiment illustrated in the drawings (see FIG. 3), the reagent metering rod 46 is slidably engaged through a vertical bore 71 provided in lens block 25, as shown. A horizontal detent chamber 72 is threadedly engaged in block 25, extending adjacent rod 46, said chamber 72 containing a friction ball 73 biased into engagement with rod 46 by a coiled spring 74 axially arranged in the chamber and bearing between said ball and the opposite end wall of the chamber. The ball 73 exerts a holding action on rod 46 sufficient to cause plunger 45 to be elevated along with plunger 21 on the upward filling stroke, but yielding to allow plunger 21 to be further elevated to its limit after block 47 has engaged its stop flange 48. On the downward dispensing stroke of plunger 21, reagent plunger 45 is returned to its lowermost position, and the yieldable connection of block 25 to rod 46 allows diluent plunger 21 to be returned to its lowermost position.

In operation, with the plungers 21 and 45 fully lowered, the tip conduit 53 is immersed in a receptacle containing the reagent to be dispensed and diluted. Handle 70 is then elevated to raise plunger 21 to its upper limit, wherein the cushion pad engages the bottom surface of flange 23. This causes ball 34 to unseat and allows the desired measured amount of diluent to be drawn into barrel 12. This also elevates plunger 45 to its upper limit by the action above described, causing the preset desired amount of reagent to be aspirated into the conduit portions 53 and 52. At the same time, the preset desired amount of diluent is drawn into barrel 12. The weighted member 63, combined with the controlled suction in barrel 12, holds the ball 55 seated during this step. The reagent vessel is then removed and the intended receiving vessel is then placed below the bottom end 54 of conduit 53. The handle 70 is then moved downwardly to bring plunger 21 to its lowermost position. This seats ball 34 and unseats ball 55, and also returns plunger 45 to its lowermost position by the action above described, discharging the measured amounts of reagent and diluent into the receiving vessel and at the same time washing out the outlet conduits 52 and 53 with diluent.

It will be noted that in the above-described apparatus, the aspirator plunger travel is limited to a distance no greater than the diluent plunger travel distance. This limitation is overcome by a proper choice of barrel diameters so that the required range of relative diluent and reagent volumes can be obtained.

During the upward filling stroke the ball 55 remains seated by the action of the weighted chamber 63 and also because the restricted diluent intake opening 35 prevents too rapid inflow of diluent into the space 29.

The operating handle 70 is provided with a hole 75 enabling it to be at times attached to a suitable spring-biased foot treadle-operated linkage, or other type of mechanical linkage, leaving the operator's hands free for manipulating the reagent supply container and the receiving vessel.

For allowing air intake into the diluent bottle 14, the tube 41 may be omitted and instead the barrel 12 may be non-sealingly clamped in the neck 13 of the bottle, and for air-filtering action a filter ring may be employed in the non-sealing clamping connection of the barrel to the neck 13.

Other types of yieldable couplings between the diluent and reagent plungers may be employed within the spirit of the present invention, such as lost-motion friction couplings, slidable connections employing permanent magnets, connections by means of suitable springs, and the like. A wide variety of such yieldable couplings will occur to those skilled in the art.

Therefore, while a specific embodiment of an improved automatic dilutor has been disclosed in the foregoing description, it will be understood that various modifications within the spirit of the invention may occur to those skilled in the art. Accordingly, it is intended that no limitations be placed on the invention except as defined by the scope of the appended claims.

What is claimed is:

1. A reagent dilutor comprising an upright diluent barrel having a lower intake portion provided with suction-responsive, upwardly-opening first check valve means and having an upper portion, means to operatively engage said intake portion in a diluent container, a diluent dispensing plunger in the upper portion of said barrel and having a lowermost position, means limiting the upward extension of said diluent dispensing plunger, a branch conduit connected to said barrel subjacent the lowermost position of the bottom end of the plunger, an upright reagent aspirating barrel, means including bottom pressure-responsive, upwardly-opening second check valve means connecting said branch conduit to the bottom end of said reagent aspirating barrel, biasing means acting on said second check valve means to prevent its opening when the diluent dispensing plunger is moved upwardly, a reagent aspirating plunger in said reagent aspirating barrel and having a lowermost position therein, means limiting the upward extension of said reagent aspirating plunger, the limited extension of the diluent plunger being greater than that of the reagent aspirating plunger, an open-ended conduit member connected to the lower portion of said reagent aspirating barrel above said second check valve means and subjacent the lowermost position of the bottom end of the reagent aspirating plunger, and means fixedly secured to one plunger and yieldably connected to the other plunger, whereby the reagent aspirating plunger will move upwardly through a reagent intake stroke when the diluent plunger is moved upwardly through a diluent intake stroke and will move downwardly through a reagent dispensing stroke when the diluent plunger is moved downwardly through a diluent dispensing stroke with the strokes of the reagent aspirating plunger being shorter than that of the diluent plunger.

2. The reagent dilutor of claim 1, and means to adjust the limit of upward extension of said diluent dispensing plunger.

3. The reagent dilutor of claim 1, and means to adjust the limit of upward extension of said reagent aspirating plunger.

4. The reagent dilutor of claim 1, and wherein said diluent barrel intake portion has a relatively restricted intake opening to retard diluent intake.

5. The reagent dilutor of claim 1, and wherein said second check valve means comprises an apertured ball seat, and a movable valve ball on said seat, and wherein said biasing means comprises a movable biasing weight member disposed on said ball to retard opening of said second check valve means.

6. The reagent dilutor of claim 1, and wherein the means limiting upward extension of said diluent dispensing plunger comprises abutment means on the diluent barrel, a rod member secured to the diluent dispensing plunger and extending parallel to said diluent barrel, and a stop member secured to said rod member and being engageable with said abutment means.

7. The reagent dilutor of claim 6, and wherein said stop member comprises a magnifying lens block overlying the diluent barrel.

8. The reagent dilutor of claim 7, and means to adjust the position of said magnifying lens block on said rod member.

9. The reagent dilutor of claim 1, and wherein the means limiting upward extension of said diluent dispensing plunger comprises first abutment means on the diluent barrel, a first rod member secured to the diluent dispensing plunger and extending parallel to said diluent barrel, and a first stop member secured to said first rod member and being engageable with said first abutment means, and wherein the means limiting upward extension of said reagent aspirating plunger comprises second abutment means on the reagent aspirating barrel, a second rod member secured to said reagent aspirating plunger and extending parallel to said reagent aspirating barrel, and a second stop member secured to said second rod member and being engageable with said second abutment means.

10. The reagent dilutor of claim 9, and wherein said second stop member comprises a magnifying lens block overlying the reagent aspirating barrel.

11. The reagent dilutor of claim 9, and wherein one of the rod members extends slidably through the stop member carried by the other rod member and the yieldable coupling means comprises means on the slidably-engaged stop member resiliently engaging the rod member extending therethrough.

12. The reagent dilutor of claim 9, and wherein the second rod member extends slidably through the first-named stop member and the yieldable coupling means comprises means on said first-named stop member resiliently engaging said second rod member.

13. The reagent dilutor of claim 12, and wherein the means resiliently engaging said second rod member comprises a spring-pressed ball element carried by said first-named stop member.

14. The reagent dilutor of claim 12, and wherein said stop members comprise respective magnifying lens blocks overlying the diluent barrel and the aspirating barrel.

15. The reagent dilutor of claim 14, and means to adjust the positions of the magnifying lens blocks on the respective rod members.

* * * * *